United States Patent
Otsuki et al.

(10) Patent No.: US 6,532,069 B1
(45) Date of Patent: Mar. 11, 2003

(54) PARTICLE-MEASURING SYSTEM AND PARTICLE-MEASURING METHOD

(75) Inventors: Hayashi Otsuki, Nakakoma-gun (JP); Tsukasa Matsuda, Kitakoma-gun (JP); Kyoko Ikeda, Kofu (JP)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 09/594,479

(22) Filed: Jun. 14, 2000

(30) Foreign Application Priority Data

Jun. 15, 1999 (JP) .......................................... 11-168968

(51) Int. Cl.[7] .............................................. G01N 21/00
(52) U.S. Cl. ........................ 356/338; 356/339; 356/342
(58) Field of Search ................................ 356/338, 337, 356/339, 340, 342

(56) References Cited

U.S. PATENT DOCUMENTS

| | | | |
|---|---|---|---|
| 5,271,264 A | | 12/1993 | Chanayem |
| 5,347,138 A | | 9/1994 | Aqui et al. |
| 5,438,526 A | | 8/1995 | Itoh et al. |
| 5,501,113 A | * | 3/1996 | Harrison et al. ............ 73/865.5 |
| 5,837,094 A | * | 11/1998 | Tsukazaki et al. ....... 118/723 R |
| 6,269,681 B1 | * | 8/2001 | Hara et al. ...................... 73/38 |

FOREIGN PATENT DOCUMENTS

| | | |
|---|---|---|
| JP | 6-110870 | 4/1994 |
| JP | 10-242060 | 9/1998 |
| JP | 11-87248 | 3/1999 |

OTHER PUBLICATIONS

Tom Winter, et al., "ISPM Characterization of Gas Phase Nucleation in a Novellus C1 WCVD Process Chamber," IEEE/SEMI Advanced Semiconductor Manufacturing Conference, 1995, pp. 17–22.

Jenny Asbell, et al., "Improving Tungsten CVD Performance with In Situ Particle Monitoring," Micro, Jul./Aug. 1997, pp. 63–73.

* cited by examiner

Primary Examiner—Frank G. Font
Assistant Examiner—Roy M. Punnoose
(74) Attorney, Agent, or Firm—Oblon, Spivak, McClelland, Maier & Neustadt, P.C.

(57) ABSTRACT

The present invention provides a particle-measuring system and the particle measuring method that is provided in a processing system for generating an atmosphere including atmospheric air or a gas exhausted from within a processing chamber by a vacuum pump, and for processing a wafer W relating to a semiconductor manufacturing in this atmosphere, and that is installed on an exhaust pipe connecting between an exhaust opening of the processing chamber and the vacuum pump, for measuring the number of particles included in the exhaust gas.

9 Claims, 13 Drawing Sheets

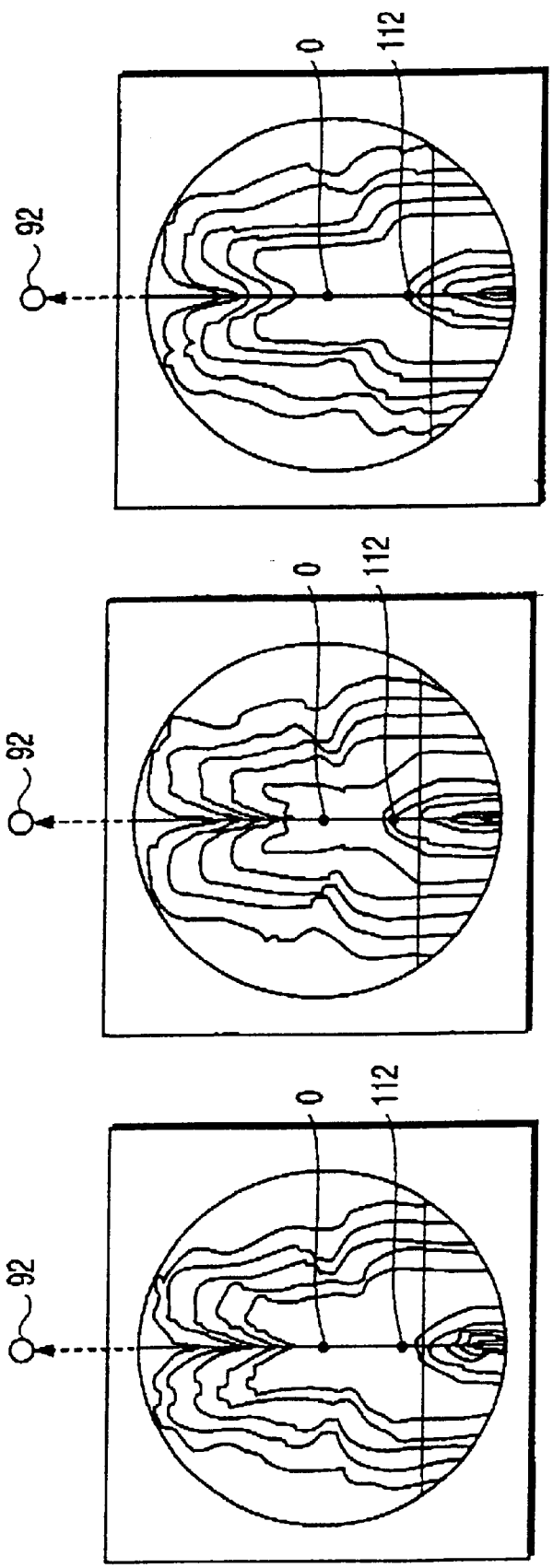

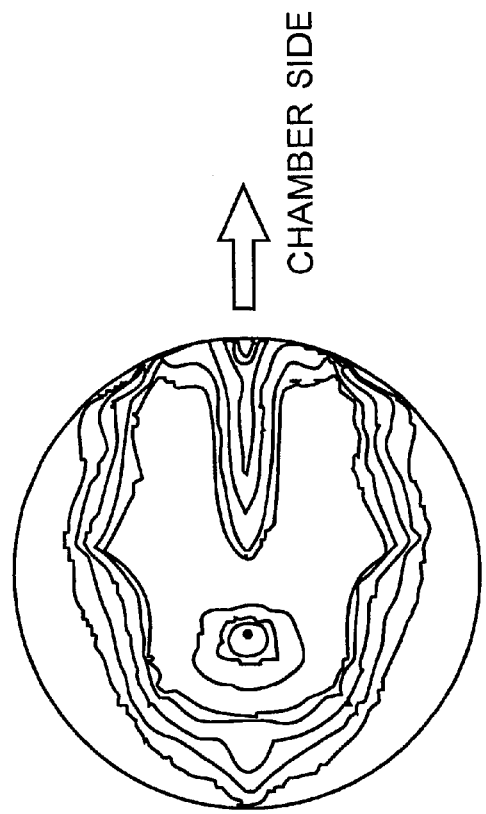
F I G. 15
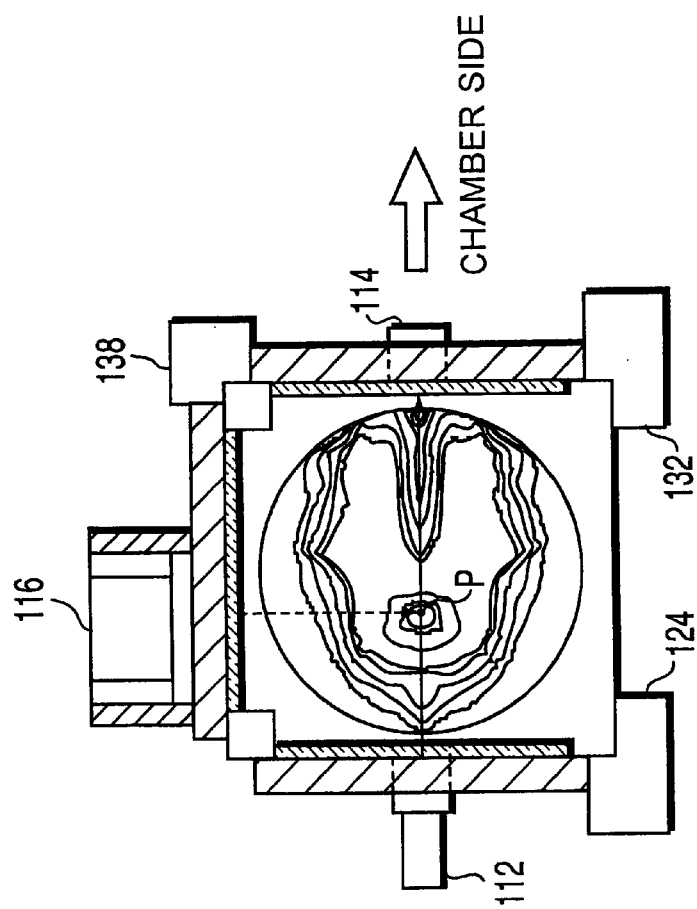
F I G. 16

PARTICLE-MEASURING SYSTEM AND PARTICLE-MEASURING METHOD

CROSS-REFERENCE TO RELATED APPLICATIONS

This application is based upon and claims the benefit of priority from the prior Japanese Patent Application No. 11-168968, filed Jun. 15, 1999, the entire contents of which are incorporated herein by reference.

BACKGROUND OF THE INVENTION

The present invention relates to a particle-measuring system that is mounted on a processing unit for forming a film on a semiconductor wafer by using a gas, and that measures the number of particles included in an exhaust gas discharged from the processing unit.

Generally, in the manufacturing of semiconductor integrated circuits, various kinds of processing units are used for processing semiconductor wafers (hereinafter to be referred to as wafers) as objects to be processed at various manufacturing stages, including a film deposition (CVD: chemical vapor deposition) process, thermal oxidation and impurity diffusion processes, an etching process, a film forming (sputtering) process, a thermal processing process, etc.

In the film forming process, thin films such as a silicon oxide ($SiO_2$) film, a silicon nitride (SiN) film, and the like are deposited as insulation layers or insulation films on the surface of the wafer using, for example, a CVD unit. For forming wiring patterns and embedding trenches, thin films of tungsten (W), tungsten silicide (WSi), titanium (Ti), titanium nitride (TiN), titanium silicide (TiSi), etc. are deposited.

When these processing systems are used to carry out each processing, it is necessary to avoid as far as possible the generation of particles that become the cause of reduction in product yield.

Therefore, a particle-measuring system is installed on the processing system in order to real-time monitor the state of generation of particles within a processing chamber or in order to know the timing for cleaning the processing chamber. Particularly, in the film-forming system such as a CVD system or a sputtering system, there occurs an adhesion of unnecessary films onto the inner wall of the processing chamber or onto the surface of the parts. These unnecessary films are disposed and accumulated within the chamber during the film-forming process. These unnecessary films are easily peeled off at the next film-forming cycle, and particles are easily generated. Therefore, it has been important to monitor the volume of particles generated during the film-forming process.

One example of a processing system having a conventional particle-measuring system will be explained with reference to FIG. 18.

A mounting table 4 for mounting a wafer W is provided inside a processing chamber 2 of almost a cylindrical shape, and a transmission window 6 made of quartz glass is disposed on the bottom of the chamber. A plurality of heating lamps 10 are disposed on a rotary table 8 below the transmission window 6. Heating beams irradiated from these heating lamps 10 are transmitted through the transmission window 6 to heat the wafer W on the mounting table 4.

A shower head 12 for introducing a processing gas such as a film-forming gas into the processing chamber 2 is provided on a chamber ceiling that faces the mounting table 4. Four exhaust openings 14 (only two openings are shown in the drawing) disposed with approximately equal intervals are provided on the periphery of the bottom of the processing chamber 2. Each of these exhaust openings 14 is connected to an exhaust pipe 16 extending downward.

Respective discharge sides of the exhaust pipes 16 are assembled into one, which is then connected to one absorption side of an assembling pipe 20 of a large diameter. A butterfly valve 18 for adjusting pressure is provided inside the assembling pipe 20. A vacuum pump 22 is provided at a discharge side of the assembling pipe 20, and a main exhaust pipe 24 of a relatively large diameter is connected to a discharge side of the vacuum pump 22. Atmospheric air and a gas within the processing chamber 2 are exhausted to the outside by this vacuum pump 22. A particle-measuring system 26 for counting the number of particles included in the exhaust gas is provided in the middle of the main exhaust pipe 24.

FIG. 19 is a diagram showing a cross-sectional configuration of the main exhaust pipe 24 provided with the particle-measuring system 26.

The particle-measuring system 26 has a laser beam irradiator 28 for emitting laser beams L and a stopper 32 for suctioning the emitted laser beams L disposed opposite to each other so that a line connecting between the two units pass through a center O of the main exhaust pipe 24. Further, a scattered light detector 30 for detecting scattered lights SL generated by a collision of the laser beams L against particles P in the middle of the irradiation of the laser beams L, is disposed facing the center O of the main exhaust pipe 24.

Based on this arrangement, for measuring the particles, the scattered light detector 30 detects the scattered lights SL that are generated when the laser beams L irradiated from the laser beam irradiator 28 have collided against the particles P that move within the main exhaust pipe 24. The particle-measuring system 26 counts the number of the particles included in the exhaust gas based on this detection.

According to the above-described conventional processing unit, the particle-measuring system 26 is provided on the main exhaust pipe 24 at the discharge side of the vacuum pump 22 that assembles the exhaust pipes 16 from the processing chamber 2 together. of course, abnormalities of products adhere onto the inner walls of the exhaust pipes and blades of the pump and the valve due to the exhaust that occurs during the process from the processing chamber 2 to the particle-measuring system 26. These adhered abnormalities are peeled off irregularly, and these generate new particles.

As the particles generated irregularly are added to the discharged particles that have actually been generated from within the processing chamber 2, it has not been possible to accurately grasp the number of particles that have been generated from within the processing chamber 2.

Further, the exhaust gas is swirled within the exhaust pipe near the discharge side of the vacuum pump 22. Therefore, the same particles cross the laser beams repeatedly, and they are counted a plurality of times.

In principle, the actual number of particles within the processing chamber 2 should be highly correlated with the count number based on the measurement of particle by the particle-measuring system 26. However, for the above reason, there is a very low correlation between the two data. Therefore, according to the conventional particle-measuring system, it has been difficult to accurately understand the state of particles actually generated from within the processing chamber 2.

BRIEF SUMMARY OF THE INVENTION

It is an object of the present invention to provide a particle-measuring system capable of grasping a state of generation of particles by keeping high correlation between the number of particles generated and exhausted from within a processing chamber and the counted number of particles based on an accurate counting of the number of particles exhausted.

The present invention provides a particle-measuring system mounted on a processing system that has a processing unit for carrying out a predetermined processing of an object to be processed and an exhaust system for exhausting an atmospheric gas from within a processing chamber of the processing unit by a vacuum pump. Within the processing system, the particle-measuring system is installed on an exhaust pipe that forms a part of the exhaust system communicating between an exhaust opening of the processing chamber and the vacuum pump. With this arrangement, the particle measuring system measures the number of the particles included in the exhaust gas discharged from within the processing chamber.

The particle-measuring system is constructed of a laser beam irradiator for irradiating laser beams to within the exhaust pipe so that the laser beams pass along a line connecting between a center point of a cross section of the exhaust pipe and a center axis passing vertically through the center of the processing chamber, and a scattered light detector provided in a direction approximately orthogonal with an irradiation direction of the laser beams, for detecting light scattered from particles.

The present invention also provides a particle-measuring method for measuring the number of particles included in an exhaust gas exhausted from a processing device for generating an atmosphere including atmospheric air or a gas exhausted from within a processing chamber by a vacuum pump, and for processing an object relating to a semiconductor manufacturing in this atmosphere, the method comprising the steps of: modeling parameters; carrying out a numerical simulation for expressing tracks of an exhaust gas that includes particles flowing through an exhaust pipe; carrying out a track numerical simulation of an exhaust gas and particles; confirming an optimum position for measuring particles; determining sensor installation position; installing the sensor; and evaluating a measurement of particle, wherein tracks of particles that flow through the exhaust pipe after the particles have been generated inside the processing chamber and exhausted from the processing chamber are simulated, to select an area where the density of the particles is the highest in the radial direction of the exhaust pipe, a laser beam irradiator is disposed at a position in this area where laser beams for measurement pass through, and a scattered-beam detector is disposed in a direction orthogonal with the laser beams, thereby to measure the particles.

The present invention further provides a particle-measuring method for measuring the number of particles included in an exhaust gas exhausted from a processing device for generating an atmospheric air or a process gas exhausted from within a processing chamber by a vacuum exhaust system, and for processing an object relating to a semiconductor manufacturing in this atmosphere, the particle measuring method using a device having a laser irradiator, a scattered-beam detector and a beam stopper for measuring the number of particles by irradiating laser beams to particles generated within the processing chamber, the particle-measuring method comprising the steps of: selecting an area in which the density of particles is high by carrying out a simulation based on information on constructional members including the processing chamber and other members disposed inside the processing chamber, information on the vacuum exhaust system, and information on the process gas; adjusting a position of the laser beam irradiator so that the laser beam irradiator can irradiate laser beams in an area in which the density of particles is high based on the simulation; adjusting a position of the beam stopper to face the laser irradiator so that the beam stopper can receive laser beams passed through the high-density area; adjusting a position of the scattered-beam detector so that the scattered-beam detector can detect scattered beams of the laser beams passed through the high-density area; irradiating by the laser irradiator the laser beams to an area in which the density of particles is high; detecting by the scattered-beam detector the scattered beams of the laser beams passed through the high-density area; and calculating the number of particles from the scattered beams detected.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 9A, 9B and 9C are diagrams showing a second example of a particle distribution according to a simulation relating to the present embodiment.

FIG. 15 is a diagram showing one example of a particle distribution state obtained by a simulation according to the second embodiment.

FIG. 16 is a diagram showing a positional relationship among a laser beam irradiator, a stopper member and a scattered light detector when the simulation data has been applied to the second embodiment.

DETAILED DESCRIPTION OF THE INVENTION

An embodiment of the present invention will be explained in detail with reference to the drawings.

Figure 1:
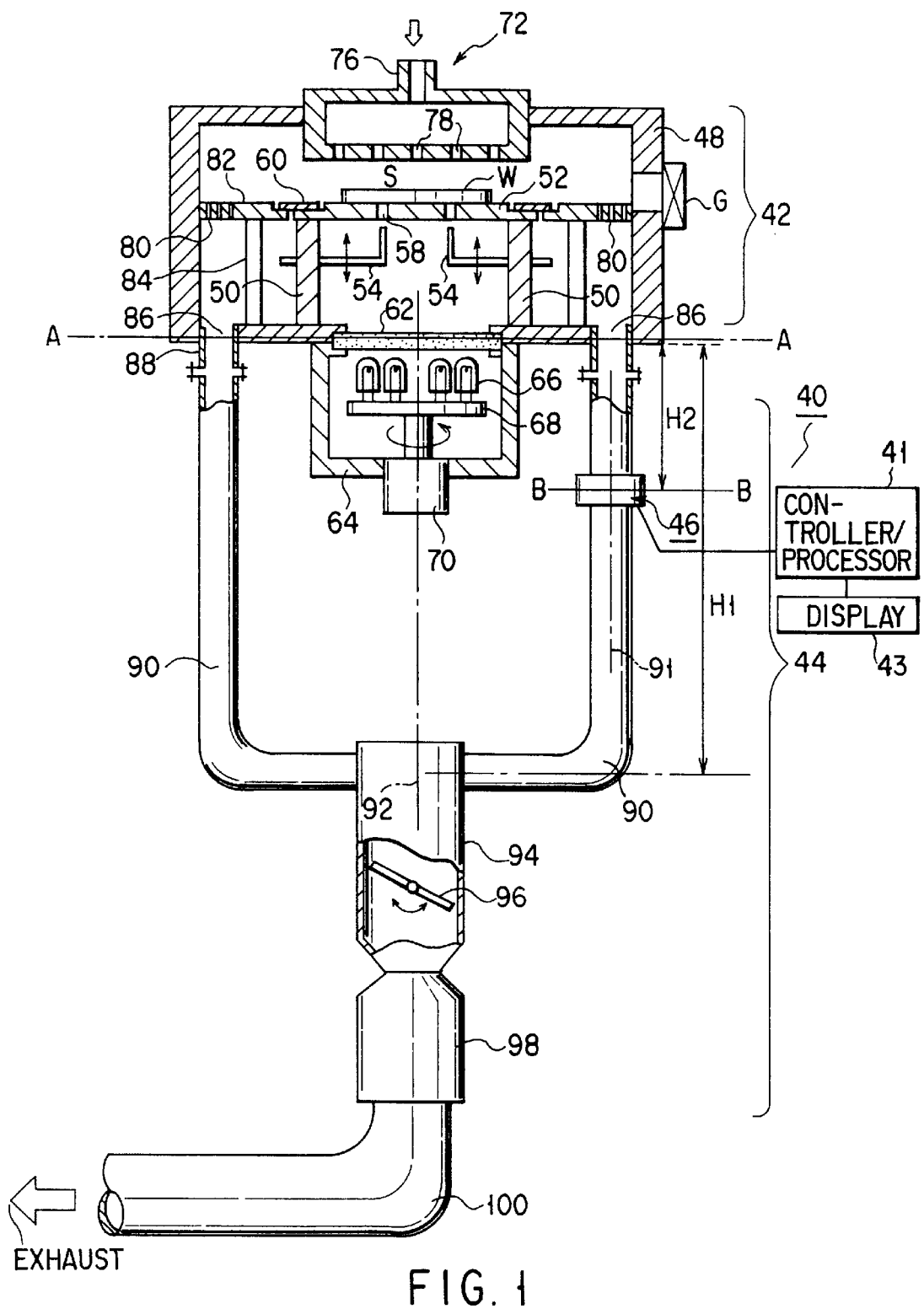
FIG. 1 is a configuration diagram showing a processing system on which a particle-measuring system relating to a first embodiment of the present invention is mounted.

FIG. 1 is a configuration diagram showing a processing system on which a particle-measuring system relating to a first embodiment of the present invention is mounted. The present embodiment will be explained by taking a CVD system as one example of a processing system for forming films on a semiconductor wafer (hereinafter to be referred to as a wafer) as an object to be processed. It is of course possible to similarly apply the particle-measuring system to other processing systems such as a sputtering system and an etching system.

The CVD system 40 is broadly constructed of a processing unit 42 for forming a film by using a film-forming gas on a wafer W, and an exhaust unit 44 for discharging atmospheric air and a film-forming gas within the processing unit 42. A particle-measuring system 46 for measuring the number of particles included in the exhaust gas flowing through the exhaust unit 44 is mounted on the CVD system 40.

The particle-measuring system 46 is controlled by a controller/processor 41 to carry out an arithmetic processing and the like. There is also provided a display 43 for making a display of processing results and expressions and various parameters to be used for simulations.

The control and process section 41 may be provided in or outside the system control section that controls the entire processing system.

This processing unit 42 has a processing chamber 48 made of aluminum (Al) in a cylindrical or boxed shape, for example. A cylindrical reflector 50 extending upward from the bottom of the processing chamber 48 is disposed within the processing chamber 48. Further, a mounting table 52 for mounting the wafer W thereon is installed on the reflector 50. This reflector 50 is formed using aluminum as a heat-ray reflective material, for example. The mounting table 52 is formed using a carbon material having a thickness of about 1 mm or an aluminum alloy such as aluminum nitride (AlN).

A plurality of lifter pins 54, for example, three lifter pins (only two lifter pins are shown in the example) that move together in up and down directions are disposed below the mounting table 52. A driving unit not shown drives the lifter pins 54 to lift the wafer W upward from the bottom surface of the mounting table 52 through lifter pin holes 58 formed on the mounting table 52. The wafer W is lifted upward by these lifter pins 54, and is carried inside the processing chamber and to the outside by a carrying mechanism having an arm or the like not shown.

A ring-shaped shield ring 60 for guaranteeing a uniform surface of a film deposited on the wafer surface is provided at the periphery of the mounting table 52.

Further, a transmission window 62 made of a heat-ray transmission material of quartz or the like is provided on the bottom of the processing chamber below the mounting table 52 to seal the chamber air-tightly. Further below this transmission window 62, there is provided a boxed-shaped heating room 64 to encircle the transmission window 62.

Within this heating room 64, a plurality of heating lamps 66 as a heat source are installed on a rotary table 68 working also as a reflection mirror. This rotary table 68 is connected to a motor by a rotary axis, and is rotated according to the rotation of the motor 70. It is possible to uniformly heat the wafer W based on this rotation.

Heat beams emitted from the heating lamps 66 are transmitted through the transmission window 62 to irradiate the bottom surface of the mounting table 52 to heat the back side of the wafer W. As the heating source, it is also possible to use a resistance-heating heater by having the resistance-heating heater embedded on the mounting table 52, in place of the heating lamps 66. Alternatively, it is also possible to heat the back side of the wafer W by blowing a heating medium such as a heated gas onto the mounting table 52.

On the ceiling of the processing chamber that faces the mounting table 52, there is provided a shower head 72 having a large number of gas injection holes 78 for introducing a processing gas such as a film-forming gas into the processing chamber 48. This shower head 72 is formed in a round box shape using, for example, aluminum or the like, and is formed with a gas introduction opening 76 for supplying a gas based on a connection to a gas introduction system not shown.

On the outer periphery of the mounting table 52, a ring-shaped rectification plate having a large number of rectification holes 80 is supported in up and down directions by a supporting column 84 formed in a ring shape. A plurality of exhaust holes 86 are formed on the bottom of the chamber below this rectification plate 82.

Figure 2:
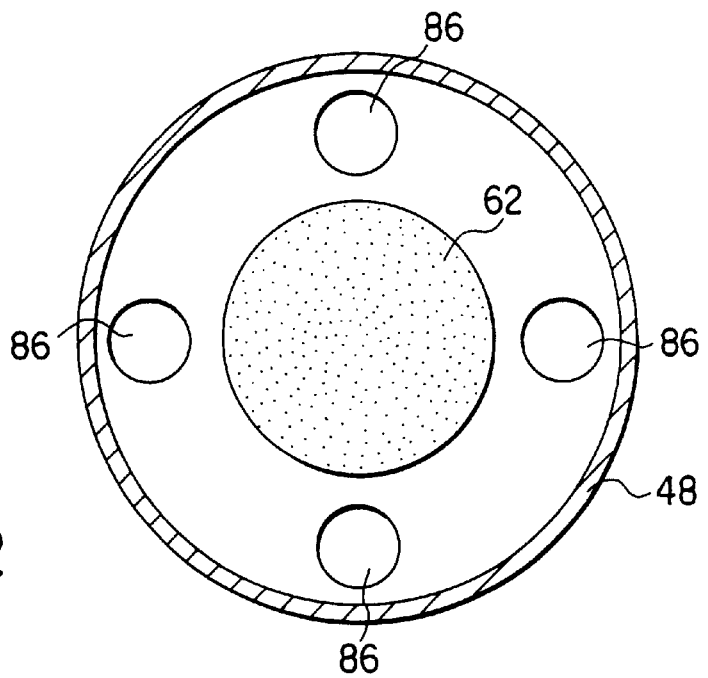
FIG. 2 is a top plan view showing a positional relationship between a transmission window and exhaust openings within a processing chamber.

FIG. 2 is a top plan view cut along a line A—A of FIG. 1 showing a positional relationship between the transmission window and the exhaust holes within the processing chamber. As shown in FIG. 2, in the present embodiment, four exhaust holes 86 are provided in approximately an equal interval along the periphery of the bottom. An exhaust pipe 88 is provided for each exhaust opening 86.

Each exhaust pipe 88 is connected in air tight to each exhaust pipe 90 that forms a part of the exhaust system 44 via a gasket based on a coupling not shown.

These exhaust pipes 90 have straight tubular shapes at the rising portions, and their discharge sides are assembled into one, which is then connected to an assembling pipe 94 having a relatively large diameter. A butterfly valve 96, for example, for adjusting the internal pressure of the processing chamber 48 is provided inside the assembling pipe 94. A vacuum pump 98 such as a turbo molecular pump is provided at a discharge side of the assembling pipe 94. A main exhaust pipe 100 of a relatively large diameter is connected to a discharge side of the vacuum pump 98. Atmospheric air and a film-forming gas within the processing chamber are exhausted to the outside from the chamber through the main exhaust pipe 100 by this vacuum pump 98.

A particle-measuring system 46 for counting the number of particles is provided in the middle of one or more of the four exhaust pipes 90 of the CVD unit.

A film-forming processing by the CVD unit of the present embodiment will be explained next.

At first, a gate valve G provided on the side wall of the processing chamber 48 is opened, and the wafer W is carried into the processing chamber 48 with a carrying arm not shown. The wafer W is delivered to the lifted lifter pins 54. Then, the lifter pins 54 are lowered to mount the wafer W on the mounting table 52. The carrying arm is then retired and the gate valve G is closed. Thereafter, the atmospheric air within the processing chamber 48 is exhausted by the exhaust system 44.

As a processing gas from a processing gas source (not shown), gases of $WF_6$ (a raw material gas), $SiH_2Cl_2$, Ar, etc. are supplied by a predetermined volume for each gas to the shower head 72, and the gases are mixed together to from the processing gas. The processing gas is then supplied approximately uniformly to within the processing chamber 48 from the gas injection holes 78.

The supplied film-forming gas is suctioned and exhausted from each exhaust opening 86 to the exhaust system 44, and the inside of the processing chamber 48 is set to a predetermined vacuum level. The heating lamps 66 are operated to emit light beams by rotating the rotary table 68 to irradiate the heating beams onto the wafer W from the back side of the mounting table 52. Thus, the wafer W is promptly heated to a predetermined level of temperature, and this temperature is maintained.

A predetermined chemical reactance of the film-forming gas occurs in the atmosphere within this processing chamber 48. As a result, tungsten silicide, for example, is deposited on the surface of the wafer W.

The film-forming gas within the processing chamber 48 flows down as an exhaust gas through each exhaust pipe 90 from each exhaust opening 86. All the exhaust gases from the exhaust pipes 90 are collected inside the assembling pipe 94. The collected exhaust gas passes through the vacuum pump 98 while being pressure-adjusted by the pressure-adjusting valve 96, and is discharged to the outside of the system from the main exhaust pipe 100. The particle-measuring system 46 counts the number of particles included in the exhaust gas.

The particle-measuring system 46 will be explained next.

Figure 3:
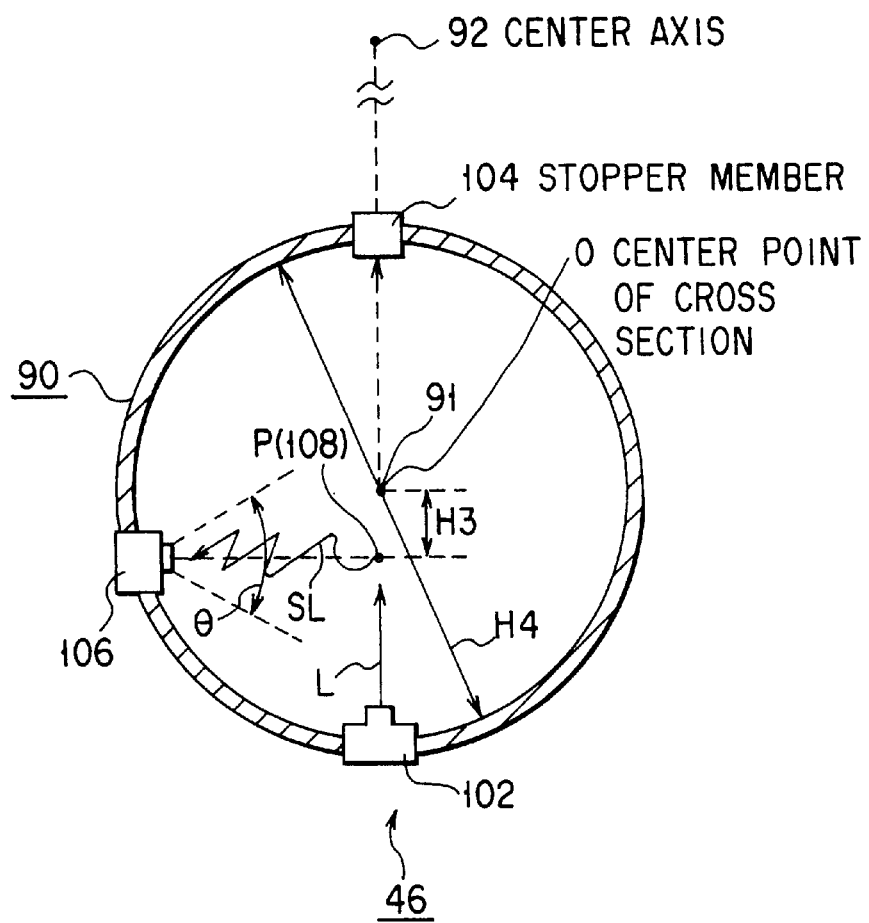
FIG. 3 is a diagram showing an installation state of the particle-measuring system.

As shown in FIG. 3, each particle-measuring system 46 consists of a laser beam irradiator 102 having a laser device for irradiating very fine laser beams L, a stopper member 104 disposed opposite to the laser beam irradiator 102 through a center axis 91 of the exhaust pipe 90, and a scattered light detector 106 of a light receiving element installed on the pipe wall in a direction approximately orthogonal with the irradiation direction of the laser beams L. The laser element described above is a semiconductor laser element which is small in size and formed of GaAlAs, for example.

The laser beam irradiator 102 is provided on the pipe wall so that the irradiated laser beams L pass along a line connecting between a center axis 92 of the chamber and a center point O of the cross section of the center axis 91 (reference FIG. 1) of the exhaust pipe 90.

The laser beams L may be irradiated in any direction so long as the irradiated laser beams L are directed to the direction in which the center axis 92 of the chamber exists through the center point O of the cross section. However, a relative positional relationship with the scattered light detector 106 is maintained.

The stopper member 104 suctions the laser beams L to avoid the generation of a diffuse reflection or the like of the laser beams L within the exhaust pipe 90.

The scattered light detector 106 made of the light receiving element or the like is provided on the pipe wall in a direction approximately orthogonal with the irradiation direction of the laser beams L as shown in FIG. 3. When the laser beams L are irradiated onto particles P (108) included in the exhaust gas, the scattered light detector 106 receives scattered lights SL that have been generated by the irradiation of the laser beams L. As described later, the center of the scattered light detector 106 is not directed toward the center point O of the cross section, but is disposed in an offset distance H3 that has been offset as shown in FIG. 3.

Figure 4:
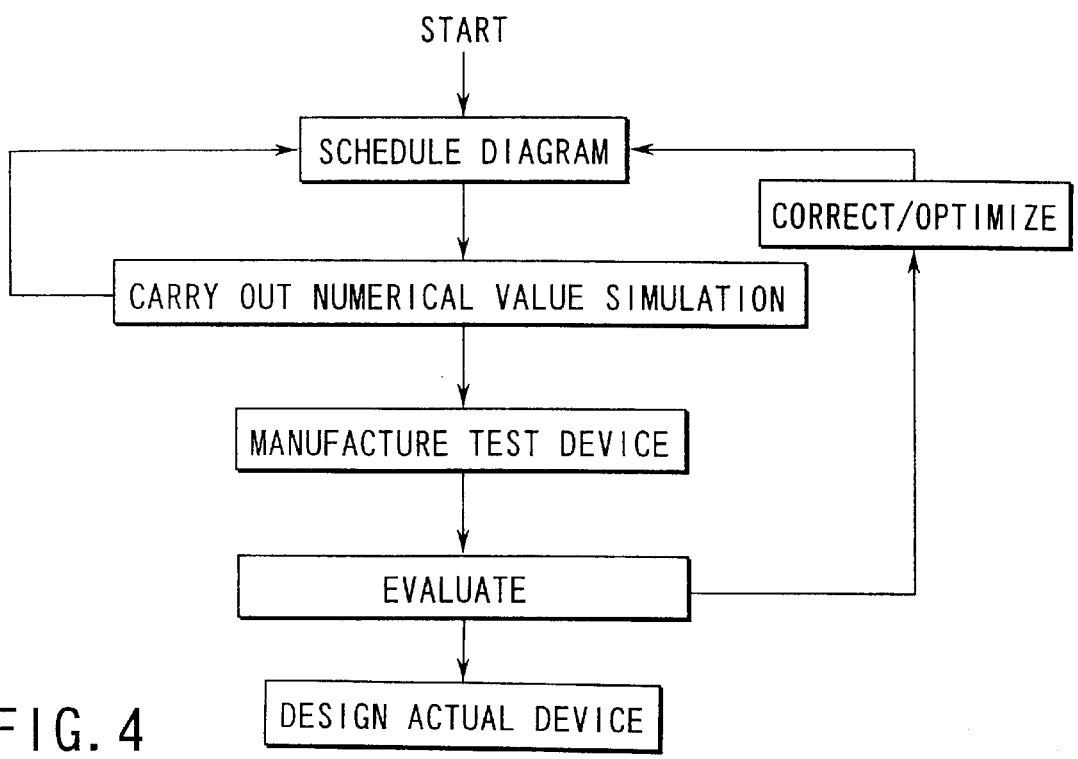
FIG. 4 is a flowchart for explaining a manufacturing of a processing system on which the particle-measuring system is to be mounted.

A position H2 for installing the particle-measuring system 46 on the exhaust pipe 90 is determined based on a computer simulation to be carried out according to a flowchart as shown in FIG. 4. One example of this computer simulation will be explained next.

First, an outline of the processing system is scheduled. Specifically, a basic system design (process conditions) including a chamber capacity, an exhaust ability, a kind of a film-forming gas, a gas supply system, a length and a diameter of an exhaust pipe, etc., is determined. Next, the installation distance H2 of the particle-measuring system 46 and the offset distance H3 are calculated according to a simulation of numerical values to be described later, and a test manufacturing of the particle-measuring system to be mounted on an actual processing system is carried out. Thus, particles are actually measured. In the evaluation of the actual measurement, when a result of the actual measurement is different from a result of the simulation or when an expected performance has not been obtained, the basic system design is corrected or optimized based on the result of the evaluation. In other words, the design is reviewed including changes in the position of installing the particle-measuring system 46, etc.

When a result of the actual measurement is satisfactory, the installation position of the particle-measuring system 46 and the offset position are reflected to a product (a processing system) on a manufacturing line.

Figure 5:
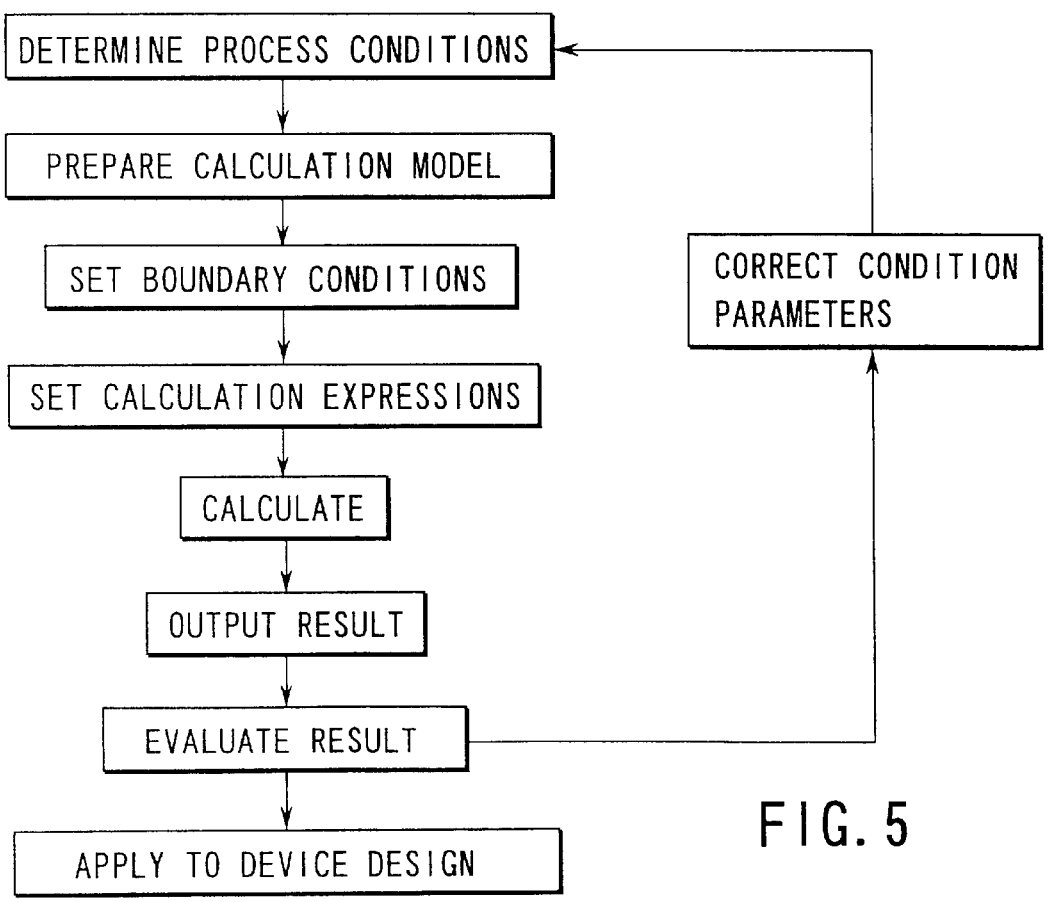
FIG. 5 is a flowchart for explaining a numerical value simulation for calculating a position of installing the particle-measuring system on the processing system.

The numerical simulation will be explained with reference to a flowchart shown in FIG. 5.

First, a calculation model (a mesh model) is prepared using computer software for calculation (for example, GAMBIT manufactured by Fluent Asia Pacific Co., Ltd.). For example, a calculation expression for setting boundary conditions (for example, a wall-surface temperature and pressure of the exhaust pipe, a kind of gas to be exhausted, etc.) is prepared based on the above-described basic system conditions (process conditions) using FLUENT of Fluent Asia Pacific Co., Ltd. This calculation is carried out. A result of the calculation is reflected to an actual system (a test system). In other words, the particle-measuring system 46 is installed on a calculated position, and a result is evaluated. When the result is satisfactory, the result is reflected to a design of a system to be manufactured.

As a result of this simulation, in the present embodiment, about 130 mm is determined as an optimum installation distance H2 from the exhaust opening 86 to the particle-measuring system 46 when a length H1 in a vertical direction is 430 mm, for example, in the exhaust pipe 90 of NW40.

For optimizing the position of installing the particle-measuring system 46, the following are the essential conditions. That is, there is no wraparound of beams generated in the processing chamber, such as, for example, heating beams (when the lamp heaters are the heating source) or plasma beams. There is space around for the installation, and that the particle-measuring system 46 is installed at a position of a relatively high density without dispersion of particles in the exhaust pipe.

Particularly, the density of the flow of an exhausted film-forming gas within the exhaust pipe is different depending on a kind of gas (a diameter and weigh of a particle), a layout shape of the exhaust pipe, a diameter of the exhaust pipe, an exhaust speed, weight, etc. Therefore, the density of particles is not necessarily high at the center of the exhaust pipe. This will be explained next.

Particles included in the exhaust gas flowing through the exhaust pipe 90 are not uniformly distributed in the gas, but tend to be unevenly distributed to an outside direction away from the center axis 92 of the processing chamber 48.

The reason is considered as follows. The film-forming gas supplied from the showerhead 72 into the processing chamber 48 flows down and is dispersed straight to the periphery of the processing chamber 48. The dispersed gas is then suctioned by each exhaust opening 86, and flows down through the exhaust pipe 90. Inertial force in a dispersion direction, that is, inertial force toward the outside in a radial direction of the processing chamber 48 applies directly to the particles.

Figure 6:
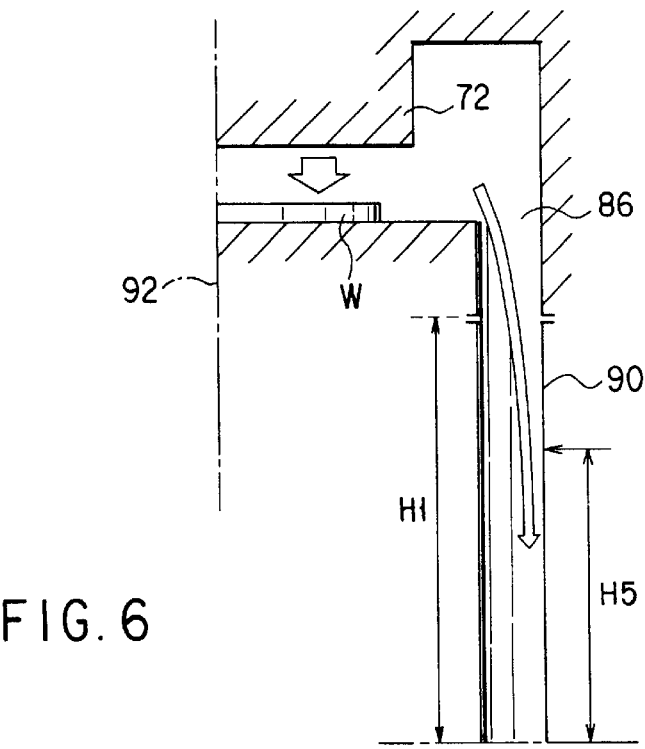
FIG. 6 is a diagram showing a model inside the processing chamber and an exhaust pipe obtained based on the simulation.

Therefore, the particles included in the exhaust gas flowing down through the exhaust pipe 90 are unevenly distributed in an outside direction away from the center axis 92 as shown in FIG. 6. As a result, the density of the particles is highest at a point of the downward offset distance H3 from the center point 0 of the cross section, as shown in FIG. 3.

FIG. 6 shows one example of a model of the exhaust pipe within the processing chamber based on the above-described simulation, for example. Referring to FIG. 6, the film-forming gas ejected from the showerhead 72 is collided against the surface of the wafer W and is dispersed to the surrounding. The dispersed gas then flows down through the exhaust pipe 90 via each exhaust opening 86. FIG. 6 shows a cross-sectional state of the distribution of the particles where the height H1 of the exhaust pipe 90 is 40 cm, a distance H5 from the bottom end of the exhaust pipe 90 is 30 cm, and the inner diameter of the exhaust pipe is 40 mm.

In this example, the exhaust gas flows down through the exhaust pipe 90, with the inertial force applied straight to the exhaust gas toward the outer peripheral direction of the processing chamber 48. Therefore, the density of the exhaust gas is considered to be higher toward the outside of the processing chamber within the exhaust pipe.

In the present embodiment, the exhaust pipe extends downwards from the bottom of the process chamber 48. Alternatively, the exhaust pipe may extend upwards from the top of the chamber 48, horizontally from one side thereof, or slantwise from any part thereof. Simulation is performed on these alternative embodiments, too.

Therefore, as shown in FIG. 3, the center of the detection direction of the scattered light detector 106 is directed outside to the center point O of the cross section of the exhaust pipe. Instead, the center of the detection direction of the scattered light detector 106 is directed to a point P (this point P is a point where the density of the particles is approximately the highest as described later) away outside from the chamber center axis 92 by a predetermined offset distance H3.

In this case, the directivity of the scattered light detector 106 has a certain level of an opening angle θ. When the scattered light detector 106 is disposed at a position with a move by the offset distance H3, the scattered light detector 106 can detect an area where the density of the particles is approximately the highest.

Although a maximum value of the offset distance H3 depends on the process conditions, this value is about 0.75 times the radius of the exhaust pipe 90 as described later. Therefore, the center of the scattered light detector 106 is set at one point in an area within the range of an outside distance from the center point O of the cross section to a point 108 shown by the distance H3.

In this example, when the diameter within the processing chamber 48 for processing an 8-inch wafer is about 440 mm and an internal diameter H4 of the exhaust pipe 90 is about 40 mm, the offset distance H3 is set at about 10 mm.

From the above, according to the present embodiment, as the particle-measuring system 46 is installed on the exhaust pipe 90 at the upstream of the vacuum pump 98, the distance of a gas route between the processing chamber 48 and the installation position of the particle-measuring system 46 becomes short. Therefore, the scattered light detector 106 can accurately detect the scattered lights SL generated based on the irradiation of the laser beams L onto the particles P as shown in FIG. 3, without detecting unnecessary particles.

As a result, it is possible to monitor the number of particles in high correlation with the actual volumes of particles within the processing chamber 48.

As shown in FIG. 3, according to the present embodiment, the laser beams L irradiated by the laser beam irradiator 102 pass through the area in which the particles tend to be highly concentrated. Further, the laser beams L are irradiated through the point P at which the particle density is the highest. Further, the center of the scattered light detector 106 is directed toward the point P at which the particle density is the highest. Therefore, it is possible to efficiently irradiate the laser beams L to the concentrated particles. Furthermore, it is possible to efficiently detect the generated scattered lights SL.

Figure 7:
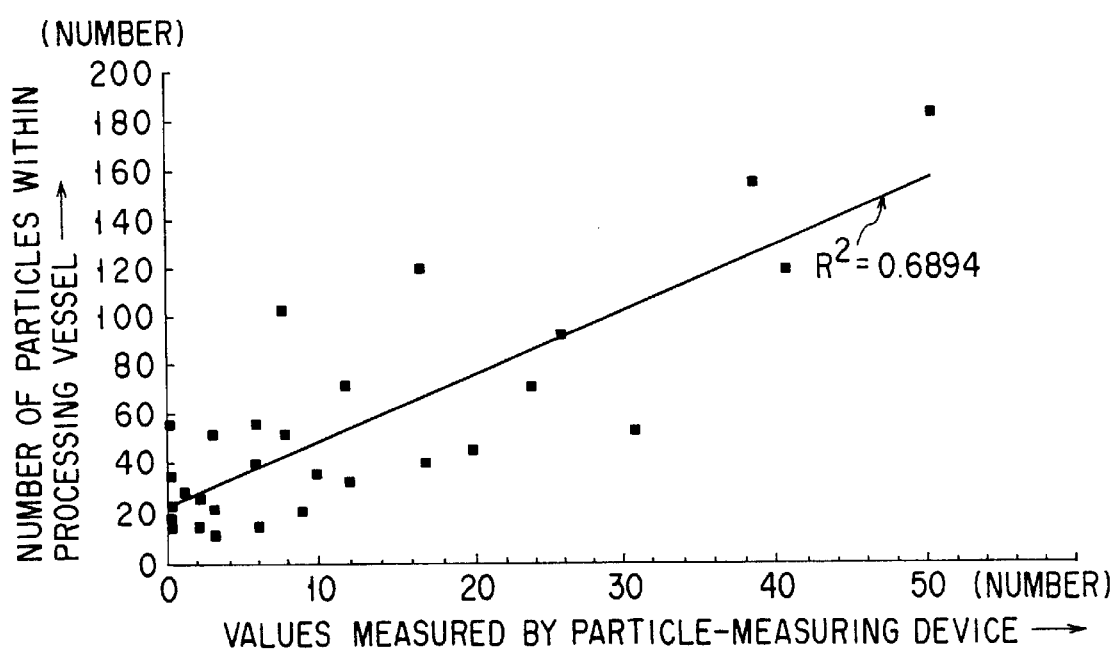
FIG. 7 is a graph showing a correlation between the number of particles within the processing chamber and the number of particles measured by the particle-measuring system.

FIG. 7 is a graph showing a correlation between the actual number of particles within the processing chamber and the number of particles measured by the particle-measuring system of the present embodiment. In this example, the diameter of particles that can be measured is 0.2 µm or above. The number of particles within the processing chamber has been obtained by measuring the number of particles on the surface of a wafer monitored by a monitor installed within the processing chamber 42. The process pressure is 0.7 Torr (93.3 Pa). As is clear from this graph, a correlation coefficient $R^2$ of the correlation between both numbers is 0.6894, and it has been confirmed that it is possible to obtain a considerably high value.

Accordingly, it is possible to detect the number of particles in higher correlation with the actual number of particles within the processing chamber 48. In this case, as the directivity of the scattered light detector 106 has a certain level of the opening angle θ, it is also possible to detect the number of particles in a high correlation when the center of the scattered light detector 106 is directed to a point deviated from the point P, for example, the center point O of the cross section.

Figure 8C:
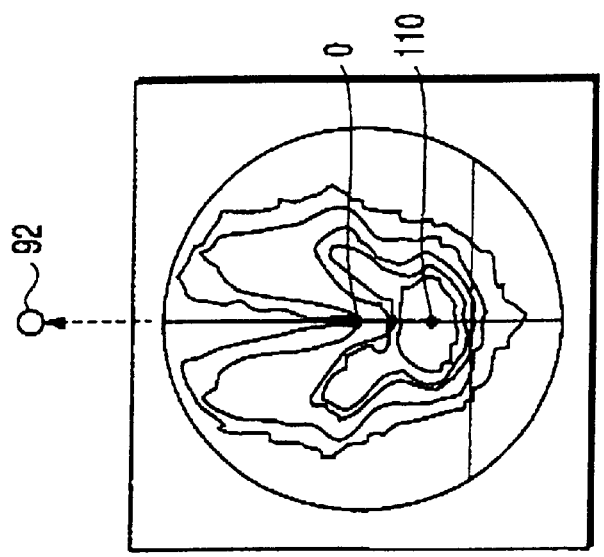
FIGS. 8A, 8B and 8C are diagrams showing a first example of a particle distribution according to a simulation relating to the present embodiment.
Figure 8B:
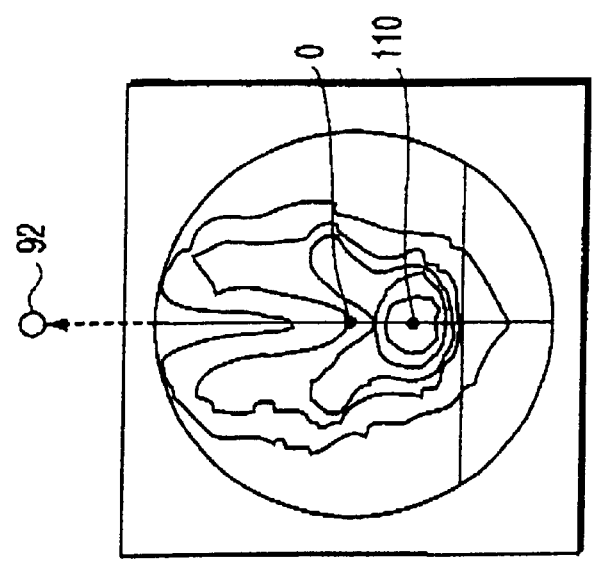
Figure 8A:
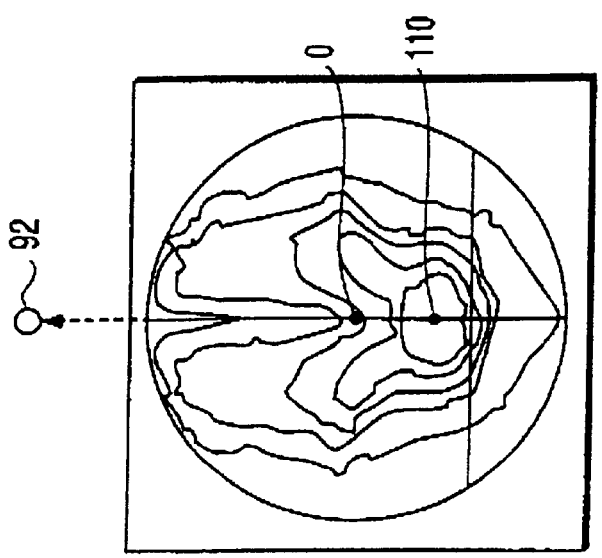

As a result of simulations, FIGS. 8A to 8C show particle distributions within the exhaust pipe when the pressure inside the processing chamber 42 is 0.7 Torr (93.3 Pa) and the film-forming temperature is 520° C. FIGS. 9A to 9C show particle distributions within the exhaust pipe when the pressure inside the processing chamber 42 is 4.5 Torr (599.8 Pa) and the film-forming temperature is 580° C. As a film-forming gas, $WF_6$, $SiH_2Cl_2$ and Ar are used. In each of these drawings, a direction in which the processing chamber center axis 92 is positioned is set above.

As shown in FIGS. 8A to 8C, when the pressure inside the processing chamber 42 is 0.7 Torr (93.3 Pa), the particles are collected in a relatively higher concentration in a direction (downward in the drawings) opposite to the direction in which the center axis 92 of the processing chamber is positioned. Particularly, the particles are concentrated at a lower position than the center point O of the cross section of the exhaust pipe. In other words, the particles are positioned in an outside direction away from the center axis 92 of the processing chamber.

This trend is the same when the diameter of the particles is 0.2 μm (FIG. 8A), 0.5 μm (FIG. 8B), and 1.0 μm (FIG. 8C). In this case, a distance between the center point O of the cross section of the exhaust pipe and a point 110 where the particle density is the highest is approximately 10 mm.

Further, as shown in FIGS. 9A to 9C, when the pressure inside the processing chamber 42 is 4.5 Torr (599.8 Pa), the particles are also collected in a relatively higher concentration in a direction (downward in the drawings) opposite to the direction in which the center axis 92 of the processing chamber is positioned. Particularly, the particles are concentrated at a lower position than the center point O of the cross section of the exhaust pipe. In other words, the particles are positioned in an outside direction away from the center axis 92 of the processing chamber. This trend is the same when the diameter of the particles is 0.2 μm (FIG. 9A), 0.5 μm (FIG. 9B), and 1.0 μm (FIG. 9C). In this case, a distance between the center point O of the cross section of the exhaust pipe and a point 112 where the particle density is the highest is approximately 15 mm.

As explained above, the center point of the particle density is slightly shifted downward in FIGS. 9A to 9C from those points shown in FIGS. 8A to 8C.

As a result of carrying out a similar simulation for each particle material of $WSi_2$, C, and Al, approximately the same distributions have been obtained. As explained above, although it depends on the process, it is possible to efficiently detect scattered lights when a particle high-density area exists within an area sandwiched between the center point O of the cross section of the exhaust pipe 90 and a point of about a maximum 15 mm away downward from this center point O and also when the center of the scattered light detector 106 (reference FIG. 3) is directed to within this area in each drawing. When the diameter of the exhaust pipe 90 is 40 mm (that is, the radius is 20 mm), the maximum 15 mm corresponds to 0.75 times the radius.

In the present embodiment, the laser beams L irradiated from the laser beam irradiator 102 have been set in a direction toward the center axis 92 of the processing chamber through the center point O of the cross section of the exhaust pipe 90. However, the setting of the laser beams L is not limited to this. The laser beams L may be set in any direction when the laser beams L are set to transmit through the area in which the particle density is high.

Figure 10:
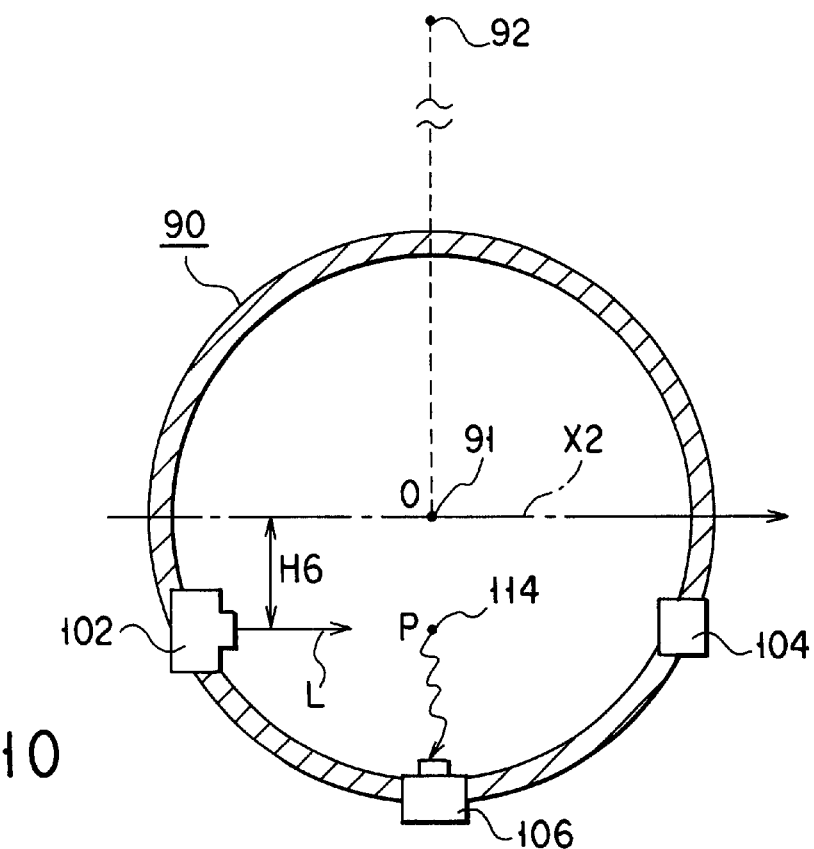
FIG. 10 is a diagram showing a modification of an installation state of the particle-measuring system in the present embodiment.

For example, as shown in FIG. 10, the laser beam irradiator 102 is set so that the laser beams L can be transmitted through a point P that is a position with a predetermined offset distance H6 from the center point 0 of the cross section of the exhaust pipe 90 to a direction opposite to the direction in which the center axis 92 of the processing chamber is positioned. In this example, the irradiation direction of the laser beams L is along a direction approximately orthogonal with a direction from the center point O of the cross section to the center axis 92 of the processing chamber. The scattered light detector 106 is set in a direction approximately orthogonal with the irradiation direction of the laser beams L. The center of the scattered light detector 106 is directed toward the point P where the density of the particles is high. As described above, a maximum value of the offset distance H6 from the center point O is 0.75 times of the radius of the exhaust pipe. In this case, the offset distance H6 is set to about 12 mm, for example.

Figure 11:
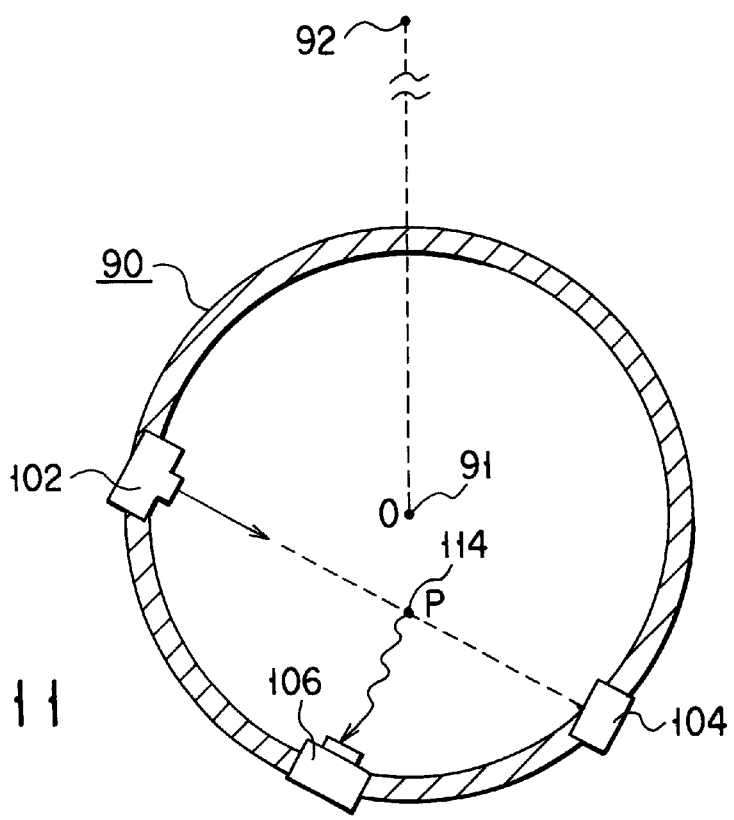
FIG. 11 is a diagram showing another modification of an installation state of the particle-measuring system in the present embodiment.

When the irradiation direction of the laser beams L passes through an area between a center point O (91) of the cross section and a point P (114), this direction is not particularly limited. For example, as shown in FIG. 11, the laser beams L may be irradiated from an inclined direction as compared with the direction shown in FIG. 10. A measurement of particles carried out based on the example of the particle-measuring system shown in FIG. 10 has been evaluated, and a result of this evaluation will be explained with reference to FIGS. 12 and 17.

Figure 12:
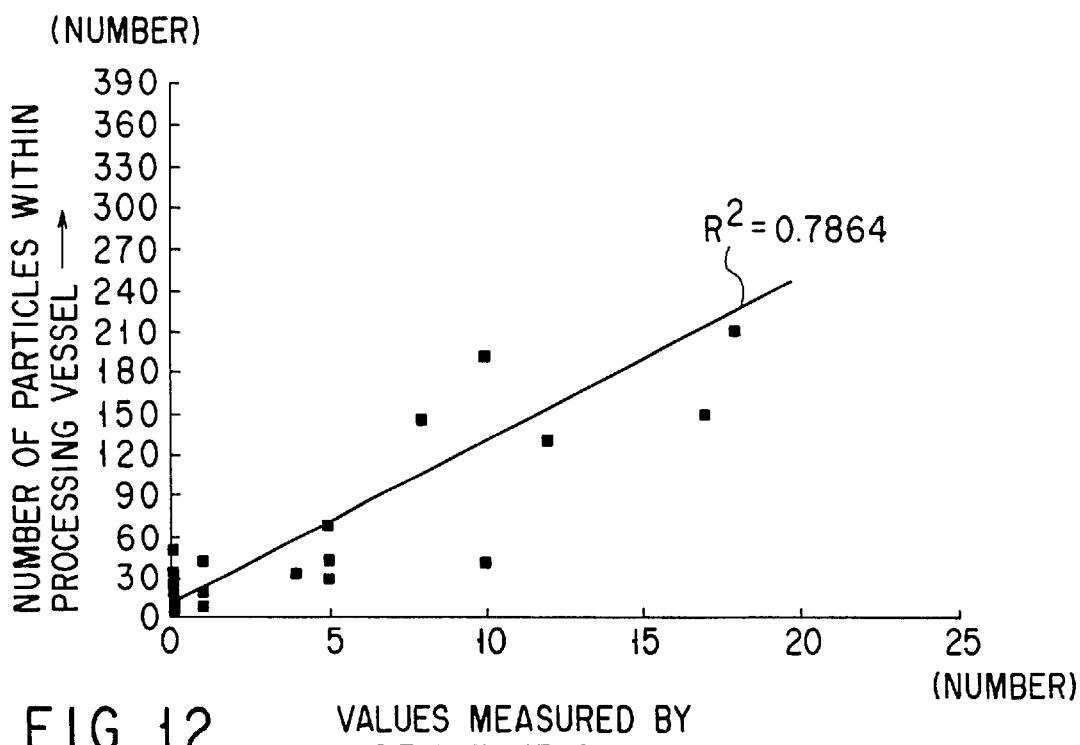
FIG. 12 is a graph showing an evaluation result of a measurement of the number of particles by passing laser beams through a portion (a point P) of a high particle density within the exhaust pipe in the particle-measuring system according to the present embodiment shown in FIG. 10.
Figure 17:
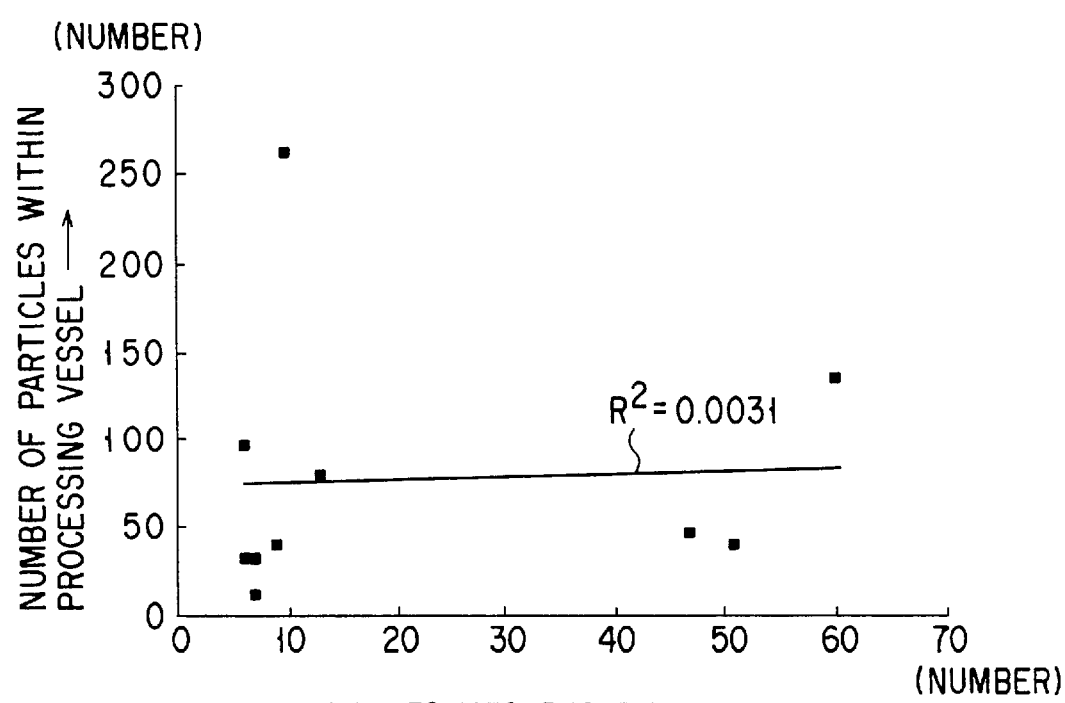
FIG. 17 is a graph showing an evaluation result of a measurement of the number of particles by passing laser beams through an exhaust pipe in a conventional particle-measuring system shown in FIG. 19.
Figure 18:
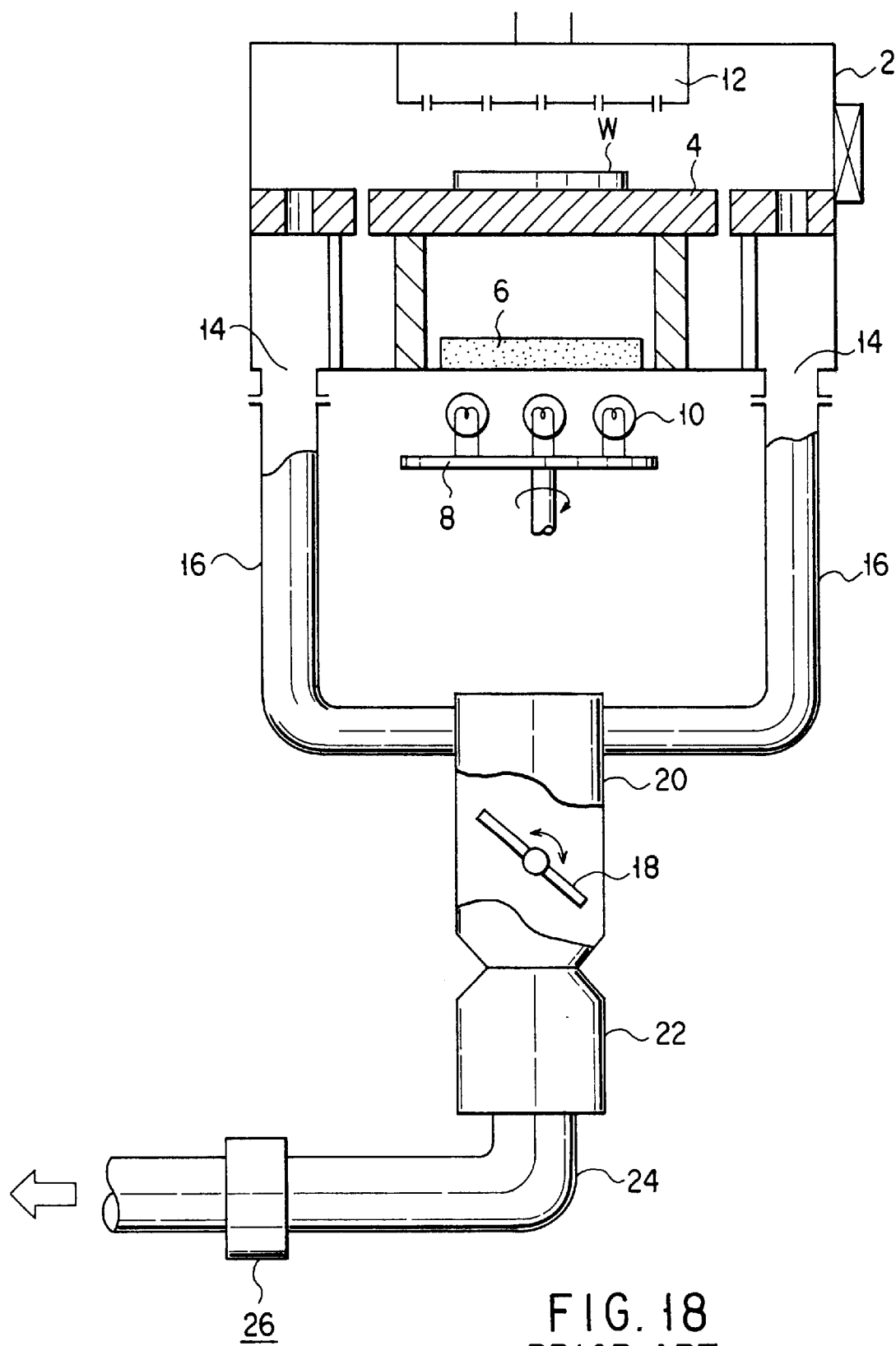
FIG. 18 is a configuration diagram showing one embodiment of a processing system on which the conventional particle-measuring system is mounted.
Figure 19:
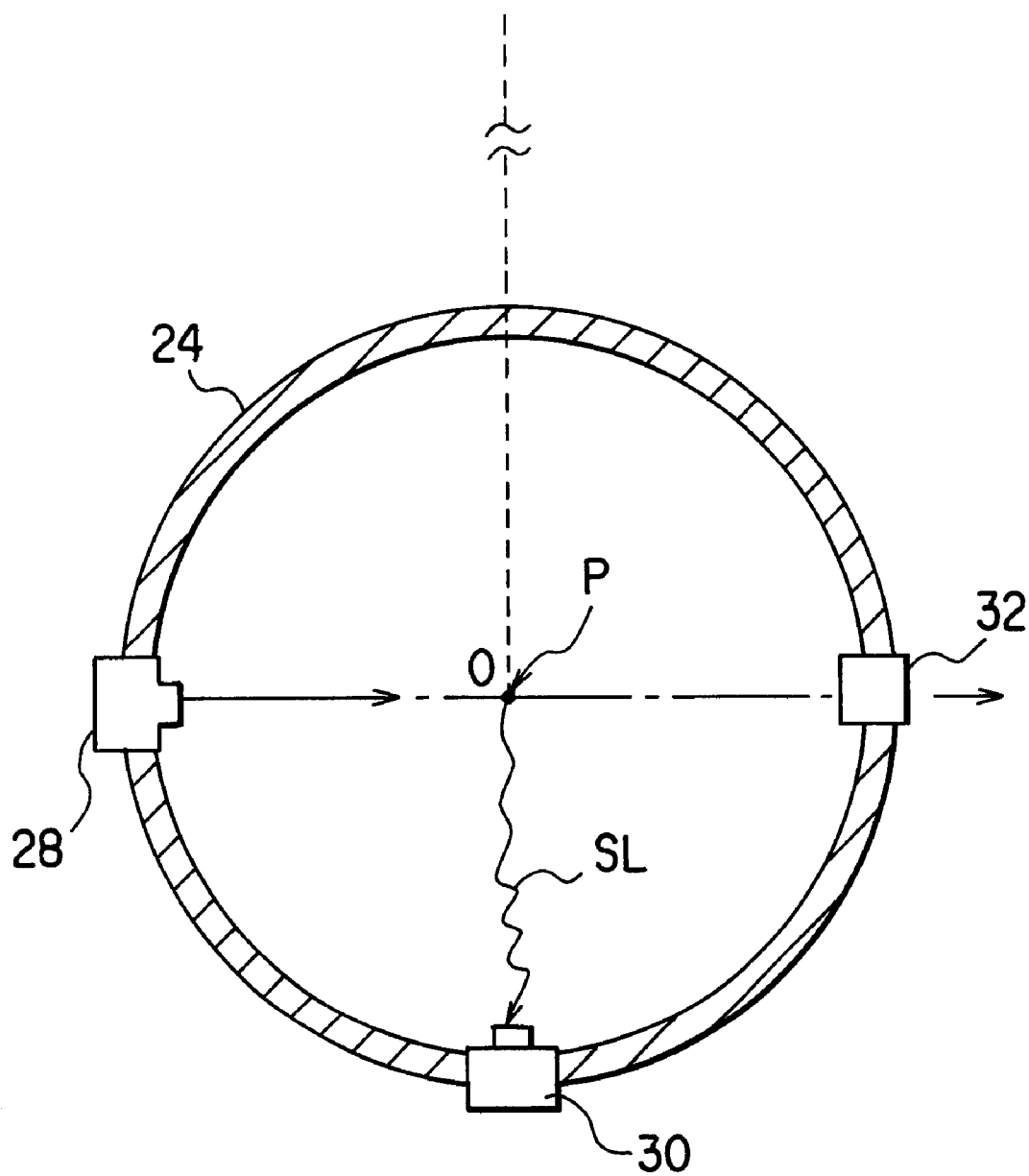
FIG. 19 is a diagram showing an installation state of the conventional particle-measuring system.

FIG. 12 is a graph showing an evaluation result of a measurement of the number of particles by passing the laser beams L through the point (the point P) where the density of the particles within the exhaust pipe is high, using the particle-measuring system according to the embodiment shown in FIG. 10. FIG. 17 is a graph showing an evaluation result of a measurement of the number of particles by passing the laser beams L through the exhaust pipe 90 using the conventional particle-measuring system shown in FIG. 18. In both cases, the particles measured have a diameter of 0.23 μm or above.

According to the present embodiment, a correlation coefficient $R^2$ becomes 0.7864 as shown in FIG. 12, which is a very high satisfactory value. On the other hand, according to the conventional particle-measuring system, a correlation coefficient $R^2$ becomes 0.0031 as shown in FIG. 17, which is a very low value.

It has been confirmed that it is possible to obtain a substantially improved high coefficient of correlation when laser beams have been passed through the portion where the density of particles is high like the present embodiment.

In the above description, a film-forming system has been explained by taking a lamp-heating system as an example. However, the film-forming system is not limited to this. It needs not be mentioned that the present invention can also be applied to a resistor-heating type film-forming system or a system using plasma. A film-forming system having a heating lamp, according to the invention has been described. Nonetheless, the invention is not limited to a film-forming system of this type. The invention can be applied to a film-forming system having a heating resistor and a film-forming system using plasma. Further, can be applied to other various processing systems such as an oxidation-diffusion system, an etching system and an annealing system. Still further, the invention can be applied to an exhaust system, such as a load lock, for use in a processing system. Further, an object to be processed is not limited to a semiconductor wafer. An LCD substrate, a glass substrate, etc. can also be processed.

As explained above, according to the processing system of the present invention, it is possible to exhibit the following excellent operation effects.

According to the present invention, as the particle-measuring system is installed on the exhaust pipe at the upstream of the vacuum pump, the distance of the gas flowing route between the processing chamber and the particle-measuring system is very short.

Therefore, unlike the conventional processing system, it is possible to avoid measuring abnormalities that fall from the inner walls of the pipes, blades of the vacuum pump and walls. Instead, it is possible to obtain a high correlation between the actual number of particles within the processing chamber and the values measured by the particle-measuring system.

Further, when the irradiation direction of the laser beams L is set to follow the direction connecting between the center point of the exhaust pipe and the center axis of the processing chamber, it is possible to irradiate the laser beams onto the portion where the density of the particles is high. Therefore, it is possible to grasp an accurate volume of particles, with a further increased correlation.

Further, when the center of the scattered light detector is offset in a predetermined direction by a predetermined distance from the center point of the cross section of the exhaust pipe, it is possible to direct the center of the scattered light detector to a portion where the density of the particles is high. As a result, it is possible to further increase the correlation.

Further, when the laser beams are transmitted to a position offset by a predetermined distance from the center point of the cross section of the exhaust pipe, it is possible to irradiate the laser beams L to a portion where the density of the particles is high. As a result, it is possible to increase the correlation.

Figure 13:
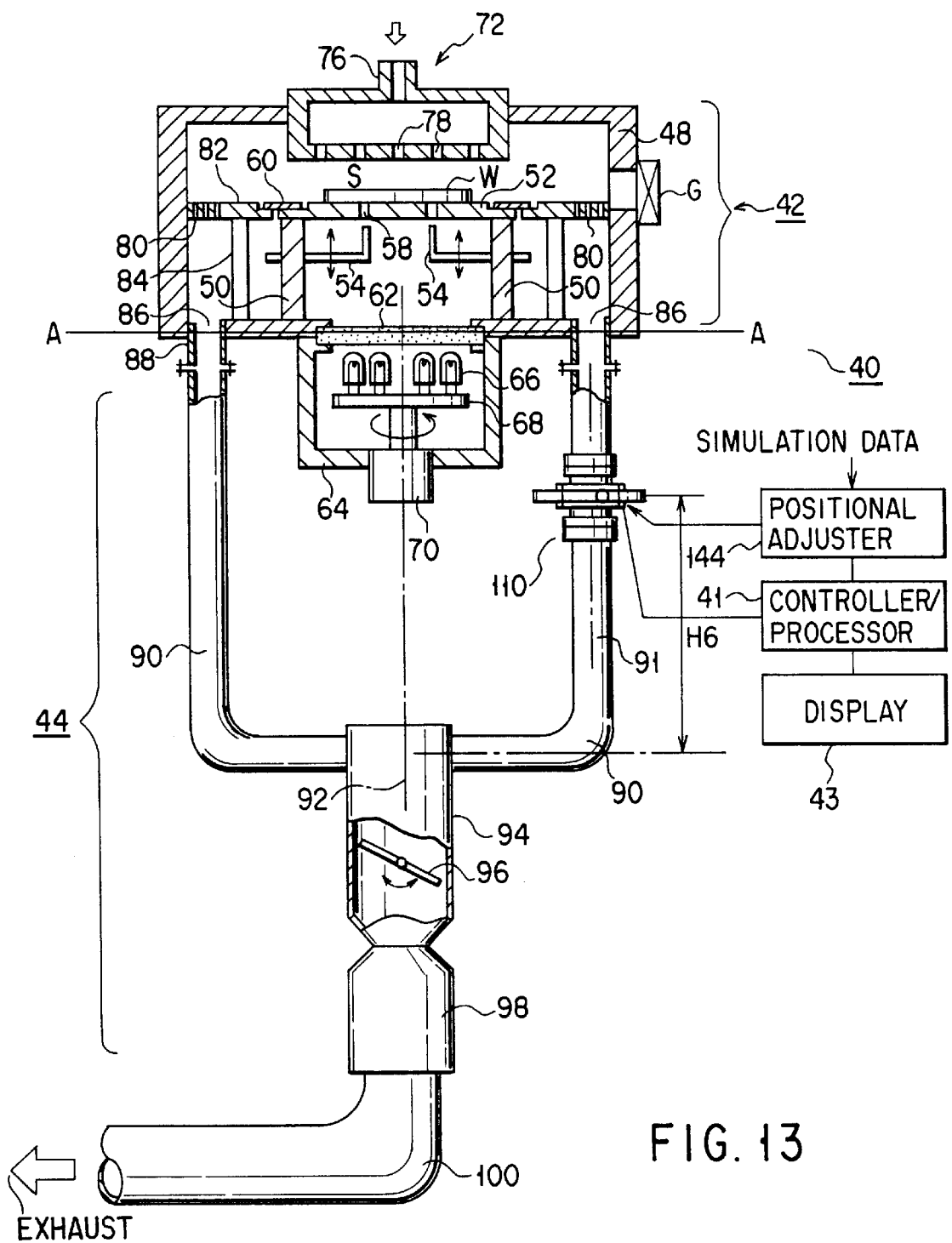
FIG. 13 is a configuration diagram showing a processing system on which a particle-measuring system relating to a second embodiment of the present invention is mounted.

FIG. 13 shows an example of a configuration of a particle-measuring system that can rotate around the piping installed, as a second embodiment of the present invention. In the configuration shown in FIG. 13, portions equivalent to those in FIG. 1 are attached with identical reference numbers, and their detailed explanation will be omitted.

A particle-measuring system 110 is installed on an exhaust pipe 90 in a similar manner to that of the particle-measuring system 46.

Figure 14A:
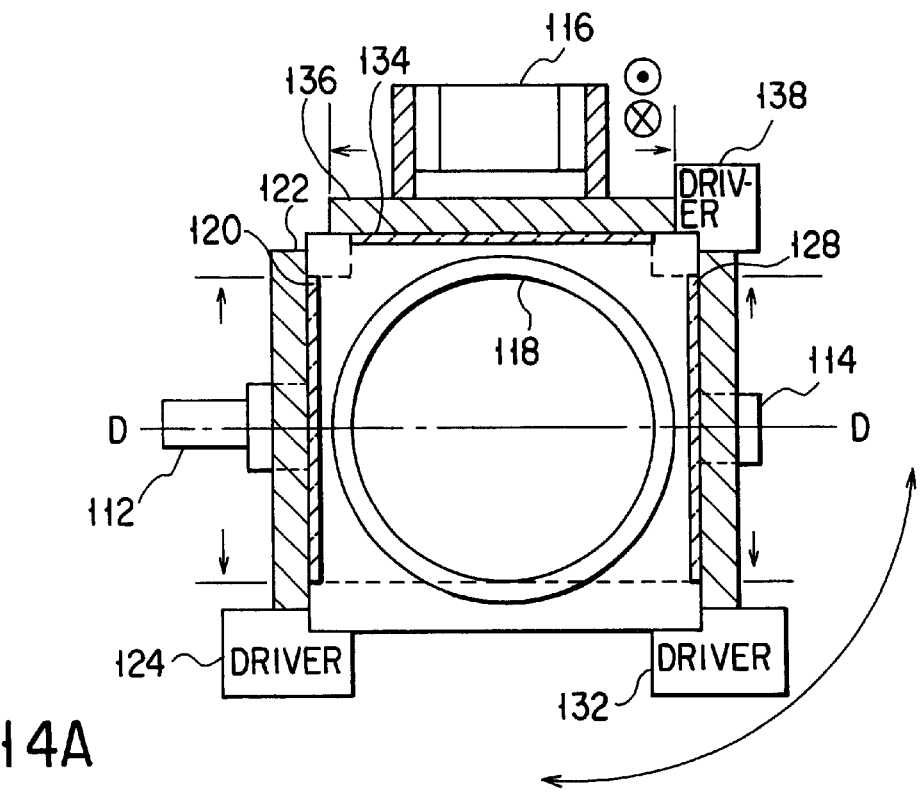
FIG. 14A and FIG. 14B are diagrams showing detailed constructions of the particle-measuring system relating to the second embodiment of the present invention.
Figure 14B:
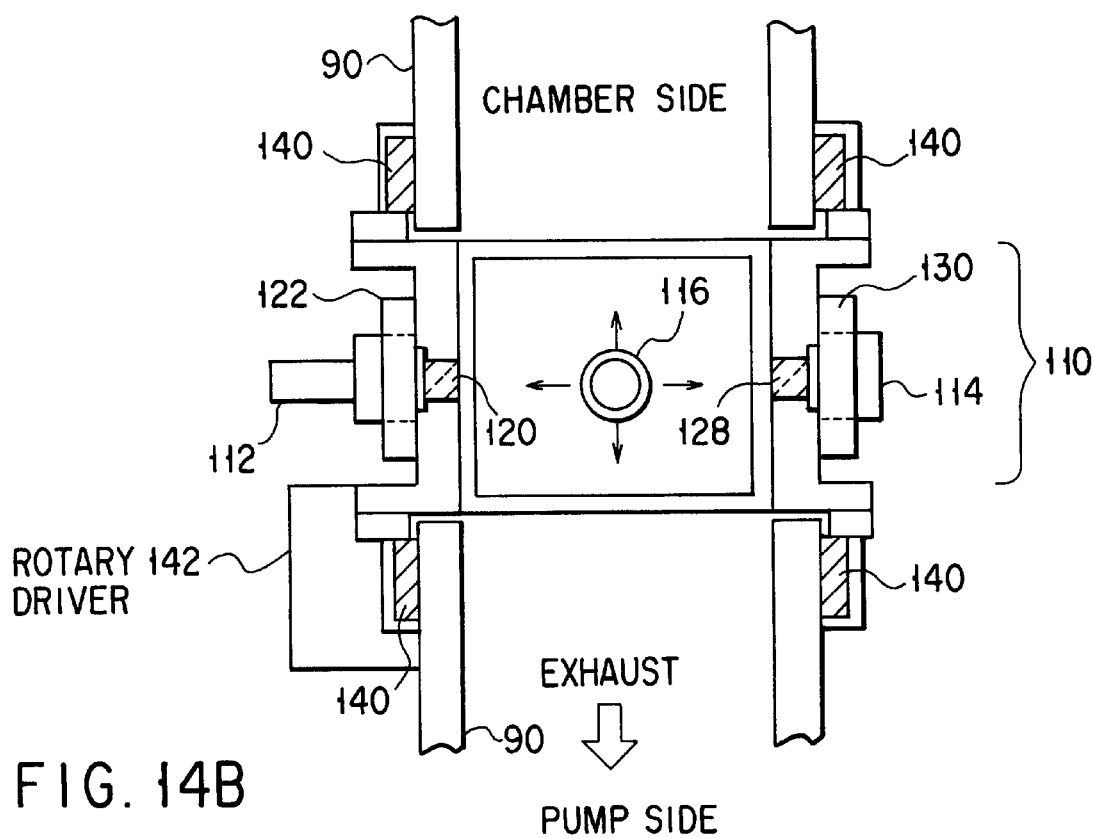

This particle-measuring system 110 consists of a stopper member 114 disposed opposite to a laser beam irradiator 112, and a scattered light detector 116 made of a light-receiving element or the like provided on the pipe wall in a direction approximately orthogonal with an irradiation direction of laser beams L, as shown in FIG. 14A. FIG. 14B is a diagram showing a configuration of a cross-sectional surface of the particle-measuring system 110 cut along a line D—D in FIG. 14A.

This laser beam irradiator 112 is disposed at the outside (atmosphere side) of a window 120 made of a transparent material provided in airtight in a radial direction of a manifold 118. A guiding mechanism 122 is provided along the window 120. The laser beam irradiator 112 is moved within the guiding mechanism 122 by a driver 124 having a motor or a linear motor.

The manifold 118 is formed using one of stainless steel, aluminum, aluminum alloy, or aluminum or aluminum alloy of which surface has been alumite processed. The window 120 is made of quartz glass or corrosion-proof sapphire glass or the like. Windows to be described later are also made of a similar material.

The stopper member 114 is also disposed at the outside of a window 128, and is always moved by a driver 132 having a motor or a linear motor to a position where laser beams irradiated by the laser beam irradiator 112 are received along a guiding mechanism 130.

The scattered light detector 116 is also moved in two-dimensional directions (up/down and left/right directions) so as to be basically in a position orthogonal with a direction of laser beams irradiated by the laser beam irradiator 112 at the outside of a window 134 provided on the manifold 118. The scattered light detector 116 is also moved to a position not orthogonal with laser beams in order to measure the number of particles at a position where the density of particles is high. The scattered light detector 116 is moved in two-dimensional directions on the window 134 by a driver 138 having a motor or a linear motor in an area encircled by a guiding mechanism 136.

As shown in FIG. 13, the particle-measuring system 110 is constructed to rotate along a radial direction of the exhaust pipe 90. Specifically, known magnetic fluid vacuum seals 140 for maintaining a vacuum state are disposed on both-end flanges, and each magnetic fluid vacuum seal 140 is fitted with the particle-measuring system 110 so as to be rotatable around the exhaust pipe 90. A rotary driver 142 executes this rotation. For example, this rotation may be carried out as follows. A gear is provided at the side of the exhaust pipe 90. A motor is connected to this gear to have an engagement with this gear. Thus, the whole particle-measuring system 110 is rotated based on the rotation of the motor. Alternatively, the particle-measuring system 110 may be rotated by magnetic force of a magnet.

For carrying out a positional adjustment of the laser beam irradiator 112, the stopper member 114 and the scattered light detector 116 respectively, a position sensor not shown is provided for each unit to detect positions. A position adjuster 144 drives each driver according to a detected position signal. Data based on a simulation may be input to this position adjuster 144 to retrieve an optimum point.

One example of a particle distribution state according to the computer simulation will be explained with reference to FIG. 15.

This simulation shows an example of exhausting a process gas of $WF_6$/DCS/Ar:4/150/450 sccm in a WSi process, with 0.7 Torr (93.3 Pa) for an internal pressure of the chamber by taking the weight into consideration. This shows a state of a result of data that a distance H3 from the center of a bent exhaust pipe connected to an assembling pipe is 300 mm.

As shown in FIG. 16, the data of this simulation is input to the position adjuster 144 to drive each driver. In this example, the laser beam irradiator 112 and the stopper member 114 are moved so that the laser beams of the laser beam irradiator 112 pass through the area in which the density of particles is highest. The scattered light detector 116 is moved to a position orthogonal with the laser beams.

The controller/processor 41 controls the laser beam irradiator 112 and the scattered light detector 116 to input measured data of particles and carry out an arithmetic processing. The control and process section 41 may be provided in or outside the system control section that controls the entire processing system. The display 43 is provided to make a display of processing results and expressions and various parameters to be used for simulations.

For example, it is possible to control and manage the controller/processor 41 and the position adjuster 144 by software by connecting these units to a user-operable controller such as a personal computer not shown.

Depending on the shape of the exhaust pipe, and also when there is a mounting table or an exhaust porous plate in front of the exhaust opening to hinder the flow of a gas, these obstacles affect the gas flow distribution within the exhaust pipe, and also affect the particle density.

Therefore, according to the present embodiment, a simulation is carried out based on parameters relating to the processing unit and the manufacturing process. Based on a result of data obtained from the simulation, the position adjuster 144 automatically moves the laser beam irradiator 112, the stopper member 114, and the scattered light detector 116, thereby to irradiate laser beams to a portion where the density of particles is the highest. Thus, the number of particles can be measured in a satisfactory condition. Particularly, it is possible to carry out a simulation and an actual measurement according to a kind of particles, or a kind of an exhaust gas including these particles, or a speed of exhausting the gas. As a result, it is possible to set an optimum measuring position.

Therefore, it is possible to find an optimum measuring point based on actual situation of measuring instead of the measuring at a constant design time. Thus, it is possible to obtain high degree of freedom of measuring and to achieve accurate measuring.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A particle-measuring method for measuring the number of particles included in an exhaust gas exhausted from a processing system for generating an atmosphere including atmospheric air or a gas exhausted from within a processing chamber by a vacuum pump, and for processing an object relating to a semiconductor manufacturing in this atmosphere, the method comprising the steps of:
    modeling a parameter regarding a principle of generating particles and a parameter representing a feature of the generated particles;
    carrying out a numerical simulation for expressing trajectory of an exhaust gas that includes particles flowing through an exhaust pipe;
    carrying out a trajectory numerical simulation of an exhaust gas and particles;
    confirming an optimum position for measuring particles;
    determining sensor installation position;
    installing the sensor; and
    counting the number of particles flowing in the exhaust pipe,
        wherein trajectory of particles that flow through the exhaust pipe after the particles have been generated inside the processing chamber and exhausted from the processing chamber are simulated, to select an area where the density of the particles is the highest in the radial direction of the exhaust pipe, a laser beam irradiator is disposed at a position in this area where laser beams for measurement pass through and a scattered light detector is disposed in a direction orthogonal with the laser beams, thereby to measure the number of the particles.

2. The particle-measuring method according to claim 1, wherein
    the step of modeling parameters comprises the steps of:
        modeling an exhaust configuration based on a shape of the chamber, a configuration of the exhaust pipe and a piping layout of the exhaust pipe;
        modeling processing conditions including a kind of a gas, a pressure, a flow rate, and temperature;
        modeling particle conditions including a composition, a density and sizes of particles generated; and
        modeling constructional members and a position for generating the particles.

3. The particle-measuring method according to claim 1, wherein the trajectory numerical simulation is obtained based on the number of openings of exhaust pipes provided in the chamber, their shapes, their layout positions, and a flow rate of the exhaust gas.

4. A particle-measuring system, provided in a processing system for generating an atmosphere including atmospheric air or a gas exhausted from within a processing chamber by a vacuum pump, and for processing an object-relating to a semiconductor manufacturing in this atmosphere,
    the particle-measuring system comprising:
        a sensor manifold installed in air-tight in front of the vacuum pipe in the middle of the exhaust pipe connected to the processing chamber, and having a rotating mechanism;
        a laser beam irradiator installed on the sensor manifold, and having a driving mechanism movable in a radial direction of the exhaust pipe;
        a beam stopper installed on the sensor manifold opposite to the laser beam irradiator, and having a driving mechanism movable in a direction to face straight the laser beam irradiator, for receiving irradiated laser beams; and
        a scattered light detector installed on the sensor manifold in a direction approximately orthogonal with the irradiation direction of the laser beams, and having a driving mechanism movable in two-dimensional directions, for detecting the laser light scattered by the particles;
        a position controller for operating the driving mechanisms of the laser beam irradiator and the beam stopper so that the laser beams pass through an area in which the density of the particles is high in the sensor manifold assumed by simulation, and for moving the scattered light detector to a position for detecting scattered lights from the high-density area; and
        a controller/processor for controlling the laser beam irradiator and the scattered light detector and for processing a measurement result obtained.

5. The particle-measuring system according to claim 4, wherein each driving mechanism has a motor or a linear motor as a driving source.

6. The particle-measuring system according to claim 4, wherein the sensor manifold is connected in airtight to the exhaust pipe so as to be rotatable around the exhaust pipe by a magnetic fluid seal.

7. The particle-measuring method according to claim 1, wherein the processing chamber has a wall, the exhaust opening is made in a given part of the wall, the exhaust pipe extends horizontally, vertically, or slantwise, and a trajectory of particles is simulated with respect to a direction in which air or gas is exhausted through the exhaust pipe.

8. A particle-measuring method for measuring the number of particles included in an exhaust gas exhausted from a processing system for generating an atmospheric air or a process gas exhausted from within a processing chamber by a vacuum exhaust system, and for processing an object relating to a semiconductor manufacturing in this atmosphere, the particle measuring method using a system having a laser irradiator, a scattered light detector and a beam stopper for measuring the number of particles by irradiating laser beams to particles generated within the processing chamber, the particle-measuring method comprising the steps of:
selecting an area in which the density of particles is high by carrying out a simulation based on information on constructional members including the processing chamber and other members disposed inside the processing chamber, information on the vacuum exhaust system, and information on the process gas;

adjusting a position of the laser beam irradiator so that the laser beam irradiator can irradiate laser beams in an area in which the density of particles is high based on the simulation;

adjusting a position of the beam stopper to face the laser irradiator so that the beam stopper can receive laser beams passed through the high-density area;

adjusting a position of the scattered light detector so that the scattered light detector can detect scattered lights of the laser beams passed through the high-density area;

irradiating by the laser irradiator the laser beams to an area in which the density of particles is high;

detecting by the scattered light detector the scattered lights of the laser beams passed through the high-density area; and calculating the number of particles from the scattered lights detected.

9. A particle-measuring method for measuring the number of particles included in an exhaust gas exhausted from a processing system for generating an atmospheric air or a gas exhausted from within a processing chamber by vacuum exhausting, the particle measuring method for measuring particles using a particle-measuring system having a laser position adjusting unit, the particle-measuring method comprising the steps of:
determining an optimum position of installing a sensor by simulation, and inputting the installation position information to a position controller of the laser position adjusting unit;

inputting processing conditions to the position controller of the laser position-adjusting unit;

adjusting by the position controller a laser beam irradiator, a scattered light detector, a beam stopper and a sensor manifold to optimum positions respectively; and measuring by the sensor particles generated within the processing chamber.

* * * * *